(12) United States Patent
Civelli

(10) Patent No.: US 8,911,857 B2
(45) Date of Patent: *Dec. 16, 2014

(54) VASCULAR STENTS

(75) Inventor: Carlo Civelli, Zurich (CH)

(73) Assignee: Axetis AG, Zug (CH)

( * ) Notice: Subject to any disclaimer, the term of this patent is extended or adjusted under 35 U.S.C. 154(b) by 292 days.

This patent is subject to a terminal disclaimer.

(21) Appl. No.: 13/362,477

(22) Filed: Jan. 31, 2012

(65) Prior Publication Data

US 2012/0130482 A1 May 24, 2012

Related U.S. Application Data

(62) Division of application No. 11/443,717, filed on May 31, 2006, now Pat. No. 8,105,374.

(30) Foreign Application Priority Data

May 31, 2005 (DE) .......... 10 2005 024 913

(51) Int. Cl.
*B32B 27/32* (2006.01)
*G11B 11/105* (2006.01)
*A61F 2/06* (2013.01)
*A61L 31/08* (2006.01)

(52) U.S. Cl.
CPC ..... *A61L 31/088* (2013.01); *A61F 2310/00011* (2013.01); *A61F 2310/00023* (2013.01); *A61F 2310/00161* (2013.01); *A61F 2310/00604* (2013.01); *A61F 2310/00616* (2013.01)
USPC .......... 428/220; 428/332; 623/1.39; 623/1.42; 623/1.44; 623/1.46

(58) Field of Classification Search
None
See application file for complete search history.

(56) References Cited

U.S. PATENT DOCUMENTS

| | | | |
|---|---|---|---|
| 4,437,192 | A | 3/1984 | Fujiu et al. |
| 6,110,204 | A | 8/2000 | Lazarov et al. |
| 6,136,156 | A | 10/2000 | El-Shall et al. |
| 6,716,444 | B1 | 4/2004 | Castro et al. |
| 7,004,975 | B2 | 2/2006 | Grundei |
| 8,105,374 | B2 * | 1/2012 | Civelli .......... 623/1.46 |
| 2002/0018851 | A1 | 2/2002 | Chang et al. |
| 2003/0050704 | A1 | 3/2003 | Keynan |
| 2003/0105516 | A1 | 6/2003 | Austin |
| 2004/0191106 | A1 | 9/2004 | O'Neill et al. |
| 2004/0243225 | A1 | 12/2004 | Ragheb et al. |
| 2005/0165487 | A1 | 7/2005 | Muhanna et al. |
| 2005/0188548 | A1 | 9/2005 | Daskal et al. |
| 2005/0209670 | A1 | 9/2005 | George et al. |
| 2007/0160639 | A1 | 7/2007 | Pantelidis et al. |

FOREIGN PATENT DOCUMENTS

| | | |
|---|---|---|
| DE | 101 23 441 A1 | 10/2002 |
| DE | 10123442 A1 | 10/2002 |
| DE | 10230720 | 2/2004 |
| DE | 10243092 A1 | 2/2004 |
| EP | 1 405 647 A1 | 4/2004 |
| WO | 00/64506 | 11/2000 |
| WO | 01/15751 A1 | 3/2001 |
| WO | 02/087648 | 11/2002 |
| WO | 03/000308 A1 | 1/2003 |

\* cited by examiner

*Primary Examiner* — Sheeba Ahmed
(74) *Attorney, Agent, or Firm* — Sughrue Mion, PLLC

(57) ABSTRACT

The disclosure describes a coating for medical implants, in particular, vascular stents, said coating comprising silicon dioxide, towards medical implants with a coating containing silicon dioxide and towards a method for their production. The coating can contain additional admixtures and have functionalization coats. The substrate of the coating is produced from a durable material, preferably from a stainless steel.

9 Claims, No Drawings

VASCULAR STENTS

BACKGROUND OF THE DISCLOSURE

The disclosure relates generally to the field of medical implants, in particular, a vascular stent, for example, for implantation in the blood vessels of a body.

BRIEF SUMMARY OF THE DISCLOSURE

So-called "stents" are deployed in vessels at risk of occlusion, for the purpose of holding open vessels, such as blood vessels (in the case of arteriosclerosis). This can either be done by means of a catheter or by means of surgically opening the vessel, clearing it out where necessary and implanting the stent. Stents are generally cylindrical, tubular structures, for example, woven fabric tubes or pipe-like porous structures, that nestle against the inner wall of a vessel and hold open an unrestricted cross-section of the flow through which the blood in the blood vessel can flow freely.

Further uses of stents are in bile ducts, airways or the esophagus. For example, stents are used in the treatment of carcinomas for the purpose of restricting the stenoses in the respiratory tract, bile ducts or esophagus after dilatation has taken place.

There is a need for medical implants, such as stents, for example, that allow easy implantation in the body of a patient.

DETAILED DESCRIPTION

Stents are deployed in vessels at risk of occlusion, for the purpose of holding open vessels, such as blood vessels (in the case of arteriosclerosis). This can either be done by means of a catheter or by means of surgically opening the vessel, clearing it out where necessary and implanting the stent. Stents are generally cylindrical, tubular structures, for example, woven fabric tubes or pipe-like porous structures, that nestle against the inner wall of a vessel and hold open an unrestricted cross-section of the flow through which the blood in the blood vessel can flow freely.

Further uses of stents are in bile ducts, airways or the esophagus. For example, stents are used in the treatment of carcinomas for the purpose of restricting the stenoses in the respiratory tract, bile ducts or esophagus after dilatation has taken place.

Stents often consist of tubes with reticular walls that have a small diameter, because of which they can easily be brought to the destination by means of a catheter, where they can be expanded with the help of a balloon (balloon catheter) in the vessel by stretching the reticular wall of the stent to the necessary lumen and therefore the diameter necessary for supporting the vessel.

It is known to coat stents with plastics, such as polytetrafluoroethylene (PTFE; TEFLON®), for example.

Inherent in known stents, however, is the problem that, because of their specific surface and their mesh structure, the body's cells often grow through or over the stents, which can, in turn, over the long run lead to a renewed occlusion of the vessel that had been secured with a stent. In this case, it is difficult to find the desired compromise between holding open the vessel and harmoniously integrating the stent into the organism. The conventional stent coatings are also not always flexible enough to go along with the stent's movements during implantation and expansion, which can result in damages to the coating. It has also been seen that an electronic potential can build up between the stent materials and the blood or other tissue, wherein such potentials can adversely modify the properties of the blood components in the layer bordering the stent materials, as a result of which uncontrolled deposits, such as plaques, can result. These problems are also found to some extent in other medical implants with similar requirements.

This need is solved by the provision of herein of coatings, medical implants, and methods for the production of a coated medical implants. Further advantageous embodiments, aspects and details of the disclosure under consideration are evident from the description herein.

An object of the present description is to provide a medical implant, such as a vascular stent, with a coating containing silicon dioxide, or, in other words, a glass-like coating. Accordingly, the disclosure is directed towards a coating for medical implants, said coating containing (i.e., including) silicon dioxide. The silicon dioxide can be present in an amorphous or crystalline or semi-crystalline form. The medical implant is preferably a vascular stent, for example, for blood vessels, bile ducts, esophagi or airways.

The properties of the coating can furthermore be modified by at least one admixture that is contained in the coating, wherein the admixture can be selected from aluminum oxide, titanium oxide, calcium compounds, sodium oxide, germanium oxide, magnesium oxide, selenium oxide and hydroxides, in particular, hydroxides of the previously mentioned metals. Particularly preferred admixtures are aluminum oxide and titanium oxide. If an admixture to silicon dioxide is used, the ratio of the admixture to the total quantity of the coating can preferably be 0.5 to 50% by weight.

In order to retain the desired surface properties across the entire surface of the medical implant, such as a vascular stent, it is preferred that the coating be essentially pore-free.

With specific embodiments, however, it can likewise be preferred that the coating have pores for functionalization with additional substances, which are applied to the coating after the actual coating process and which deposit in the pores. Accordingly, the coating described herein can have an additional functionalization coat, even applied only partially or at selective points. Such a coat can correspond to the medical purpose of the medical implant and comprise an influencing of the growth of surrounding tissue, a killing off of unwanted tissue, building up a relationship between the medical implant and tissue, etc. The functionalization coat can, for example, contain a medicine, a cell poison, or both.

A major advantage of the medical implants described herein is to be seen in that the coating can be applied in an extremely thin layer, namely, preferably in the nano-range, meaning in the range of single atom layers, which permits the final dimensions essentially to be selected during the production of the medical implant without it being necessary to take into account dimensioning changes caused by the coating that may not be predictable with precision. The thickness of the coating described herein is preferably 0.1 to 1000 nm, but it is understood that both thinner and thicker coatings are possible. Decisive in the selection of the layer thickness is the requirement that the coating not be damaged during the expansion of the implant in the body and that no additional pores be formed.

The coating can be applied in a single step, and thereby form a single layer, but can, in a preferred embodiment, also consist of multiple, successively applied layers. In the multilayer method, the composition of each individual layer can be defined separately.

This disclosure is furthermore directed towards a medical implant that has a substrate that forms a basic structure and a coating applied to at least sections of the substrate, wherein this coating contains silicon dioxides or is made of silicon dioxides. In particular, the coating is a coating described herein.

The medical implant is preferably a vascular stent. The vascular stent can be intended for a blood vessel, a bile duct, the esophagus or the trachea, wherein it can be deployed for various types of animals, such as humans, pets and production animals.

The substrate is preferably constructed from a difficult-to-degrade material, whereby "difficult-to-degrade" is taken to mean a property in which the material shows no visible signs of degrading for at least one year after implantation in a body.

For medical implants, particularly vascular stents, the substrate can comprise customary materials, such as carbon, PTFE, DACRON®, metal alloys or PHA, wherein steel alloys in particular are preferred materials. The metal alloys that can be deployed for the substrate are preferably selected from stainless steels. A further preferred material for the substrate is a shape memory metal, in particular, nickel titanium alloys, which are used for stents because of their faculties for independent shape modification.

This disclosure is likewise directed towards a method for the production of a medical implant, in particular of a medical implant described herein, the method having the steps of provision of a substrate forming the basic structure and application of a coating containing silicon dioxide by means of a plasma coating method. All that has been disclosed with regard to the coating or the medical implant also applies analogously to the methods described herein and vice versa, so that these are referred to alternately.

In order to obtain the desired pores for holding means of functionalization in certain embodiments, it is furthermore preferred that the method comprises the step of producing the pores in the coating by means of neutron bombardment. For this purpose, neutron sources, such as particle accelerators, for example, can be used. A further variant for producing the function pores consists of manufacturing the pores by means of laser light.

The subject matter disclosed herein includes a coating for medical implants, in particular vascular stents, which, because of its inert, glass-like surface with silicon dioxide, largely prevents the growth of cells of the body or attachment of such cells, which, because of its hardness, counteracts damage when the implant is introduced into the body, therefore simplifying the handling, which, because of the thinness of the coating, permits a simpler design of the implant, has reduced friction as a result of low roughness levels and therefore a smaller impact on blood components and lower coagulation formation and in which there is no degradation of the coating whatsoever, even after a longer stay in the body.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A coating for a medical implant, the coating comprising silicon dioxide, wherein the thickness of the coating is from 0.1 to 1000 nanometers.

2. The coating of claim 1, wherein the medical implant is a vascular stent.

3. The coating of claim 1, wherein the coating further comprises at least one ingredient selected from the group consisting of aluminum oxide, titanium oxide, calcium compounds, sodium oxide, germanium oxide, magnesium oxide, selenium oxide, aluminum hydroxide, titanium hydroxide, sodium hydroxide, germanium hydroxide, magnesium hydroxide, selenium hydroxide, and mixtures of these.

4. The coating of claim 3, wherein coating comprises the ingredient in an amount of approximately 0.5 to 50% by weight of the coating.

5. The coating of claim 1, wherein the coating is essentially free of pores.

6. The coating of claim 1, wherein the coating includes pores.

7. The coating of claim 1, wherein the coating further comprises a functionalization coat.

8. The coating of claim 7, wherein the functionalization coat comprises at least one of a medicine and a cell poison.

9. The coating of claim 1, wherein the coating includes multiple layers.

* * * * *